(12) United States Patent
Faivre et al.

(10) Patent No.: US 9,194,791 B2
(45) Date of Patent: Nov. 24, 2015

(54) SYSTEM FOR DETERMINING COEFFICIENTS OF SEAL FRICTION

(71) Applicant: Caterpillar Inc., Peoria, IL (US)

(72) Inventors: Joseph Faivre, Edelstein, IL (US); Yongliang Zhu, Dunlap, IL (US); Drew A. Fehr, Washington, IL (US)

(73) Assignee: Caterpillar Inc., Peoria, IL (US)

( * ) Notice: Subject to any disclaimer, the term of this patent is extended or adjusted under 35 U.S.C. 154(b) by 388 days.

(21) Appl. No.: 13/654,817

(22) Filed: Oct. 18, 2012

(65) Prior Publication Data

US 2014/0109647 A1    Apr. 24, 2014

(51) Int. Cl.
*G01N 19/02* (2006.01)
*B60T 8/172* (2006.01)

(52) U.S. Cl.
CPC ............ *G01N 19/02* (2013.01); *B60T 8/172* (2013.01); *B60T 2210/12* (2013.01)

(58) Field of Classification Search
CPC ................................................. F16K 37/0083
USPC ................................................................ 73/9
See application file for complete search history.

(56) References Cited

U.S. PATENT DOCUMENTS

| 3,717,025 | A | | 2/1973 | Kronenberg et al. |
| 4,029,122 | A | * | 6/1977 | Jaegtnes .................... 137/551 |
| 5,385,393 | A | | 1/1995 | Tanaka et al. |
| 6,056,008 | A | * | 5/2000 | Adams et al. ............ 137/487.5 |
| 6,203,121 | B1 | * | 3/2001 | Kato et al. ................... 303/150 |
| 6,745,084 | B2 | * | 6/2004 | Boger et al. .................. 700/13 |
| 7,039,537 | B2 | * | 5/2006 | Junk .............................. 702/77 |
| 7,089,086 | B2 | * | 8/2006 | Schoonover ................ 700/275 |
| 8,078,351 | B2 | | 12/2011 | Nardi et al. |
| 2008/0307783 | A1 | * | 12/2008 | Harber et al. ................ 60/426 |

* cited by examiner

*Primary Examiner* — Hezron E Williams
*Assistant Examiner* — Mark A Shabman
(74) *Attorney, Agent, or Firm* — Leydig, Voit & Mayer, Ltd.

(57) ABSTRACT

A system for determining a hydraulic seal coefficient of friction of a hydraulic cylinder includes a force sensor to provide a force signal indicative of a force of the cylinder. A controller is configured to receive a plurality of first force signals at a first load and determine a first friction force and receive a plurality of second force signals at a second load and determine a second friction force. A hydraulic seal coefficient of friction is determined based at least in part upon the first friction force and the second friction force. A method is also disclosed.

17 Claims, 8 Drawing Sheets

SYSTEM FOR DETERMINING COEFFICIENTS OF SEAL FRICTION

TECHNICAL FIELD

This disclosure relates generally to machines having hydraulic cylinders and, more particularly, to a system for determining the coefficients of friction of the seals of a hydraulic cylinder.

BACKGROUND

Many machines utilize implement systems to move a payload from one location to another. The implement systems often include one or more hydraulic cylinders to cause the movement of the implement system. Payload control or estimation systems have been developed to measure the payload being carried by the implement system. Some payload estimation systems utilize forces measured at one or more of the hydraulic cylinders as part of the payload estimation system.

The force measured at a hydraulic cylinder may not accurately reflect the load on the hydraulic cylinder due to friction of the cylinder. The friction associated with the hydraulic cylinder is generally composed of three components, namely Coulomb friction, viscous friction, and friction from the seals within the hydraulic cylinder. The friction of the seals of a hydraulic cylinder generally varies with the pressure of the hydraulic cylinder.

U.S. Pat. No. 3,717,025 discloses a method of determining static and dynamic coefficients of friction by using a testing apparatus. The apparatus uses a pivoting disc and equating the static and dynamic coefficients of friction to a torque read-out based upon the pivoting disk.

The foregoing background discussion is intended solely to aid the reader. It is not intended to limit the innovations described herein, nor to limit or expand the prior art discussed. Thus, the foregoing discussion should not be taken to indicate that any particular element of a prior system is unsuitable for use with the innovations described herein, nor is it intended to indicate that any element is essential in implementing the innovations described herein. The implementations and application of the innovations described herein are defined by the appended claims.

SUMMARY

A system for determining a hydraulic seal coefficient of friction of a hydraulic cylinder includes a linkage member for moving a load, a hydraulic cylinder operatively connected to the linkage member for moving the linkage member along a path, and a force sensor configured to provide a force signal indicative of a force of the cylinder. A controller is configured to receive a plurality of first load first direction force signals as the linkage member is moved along the path in a first direction and the linkage member engages a first load, and to receive a plurality of first load second direction force signals as the linkage member is moved along the path in a second direction, the second direction being generally opposite the first direction. The controller is further configured to determine a first friction force based at least in part upon a difference between the plurality of first load first direction force signals and the plurality of first load second direction force signals. The controller is also configured to receive a plurality of second load first direction force signals as the linkage member is moved along the path in the first direction and the linkage member engages a second load, and to receive a plurality of second load second direction force signals as the linkage member is moved along the path in the second direction and the linkage member engages the second load. The controller is configured to determine a second friction force based at least in part upon a difference between the plurality of second load first direction force signals and the plurality of second load second direction force signals, and to determine a hydraulic seal coefficient of friction based at least in part upon the first friction force and the second friction force.

In another aspect, a controller implemented method of determining a hydraulic seal coefficient of friction of a hydraulic cylinder includes receiving a plurality of first load first direction force signals as a linkage member is moved along a path in a first direction and the linkage member engages a first load, and receiving a plurality of first load second direction force signals as the linkage member is moved along the path in a second direction, the second direction being generally opposite the first direction. A first friction force is determined based at least in part upon a difference between the plurality of first load first direction force signals and the plurality of first load second direction force signals. A plurality of second load first direction force signals are received as the linkage member is moved along the path in the first direction and the linkage member engages a second load, and a plurality of second load second direction force signals are received as the linkage member is moved along the path in the second direction and the linkage member engages the second load. A second friction force is determined based at least in part upon a difference between the plurality of second load first direction force signals and the plurality of second load second direction force signals, and a hydraulic seal coefficient of friction is determined based at least in part upon the first friction force and the second friction force.

In still another aspect, a machine includes a prime mover, a linkage member for moving a load, a hydraulic cylinder operatively connected to the linkage member for moving the linkage member along a path, and a force sensor configured to provide a force signal indicative of a force of the cylinder. The hydraulic cylinder is operatively connected to the prime mover. A controller is configured to receive a plurality of first load first direction force signals as the linkage member is moved along the path in a first direction and the linkage member engages a first load, and to receive a plurality of first load second direction force signals as the linkage member is moved along the path in a second direction, the second direction being generally opposite the first direction. The controller is further configured to determine a first friction force based at least in part upon a difference between the plurality of first load first direction force signals and the plurality of first load second direction force signals. The controller is also configured to receive a plurality of second load first direction force signals as the linkage member is moved along the path in the first direction and the linkage member engages a second load, and to receive a plurality of second load second direction force signals as the linkage member is moved along the path in the second direction and the linkage member engages the second load. The controller is configured to determine a second friction force based at least in part upon a difference between the plurality of second load first direction force signals and the plurality of second load second direction force signals, and to determine a hydraulic seal coefficient of friction based at least in part upon the first friction force and the second friction force.

DETAILED DESCRIPTION

Figure 1:
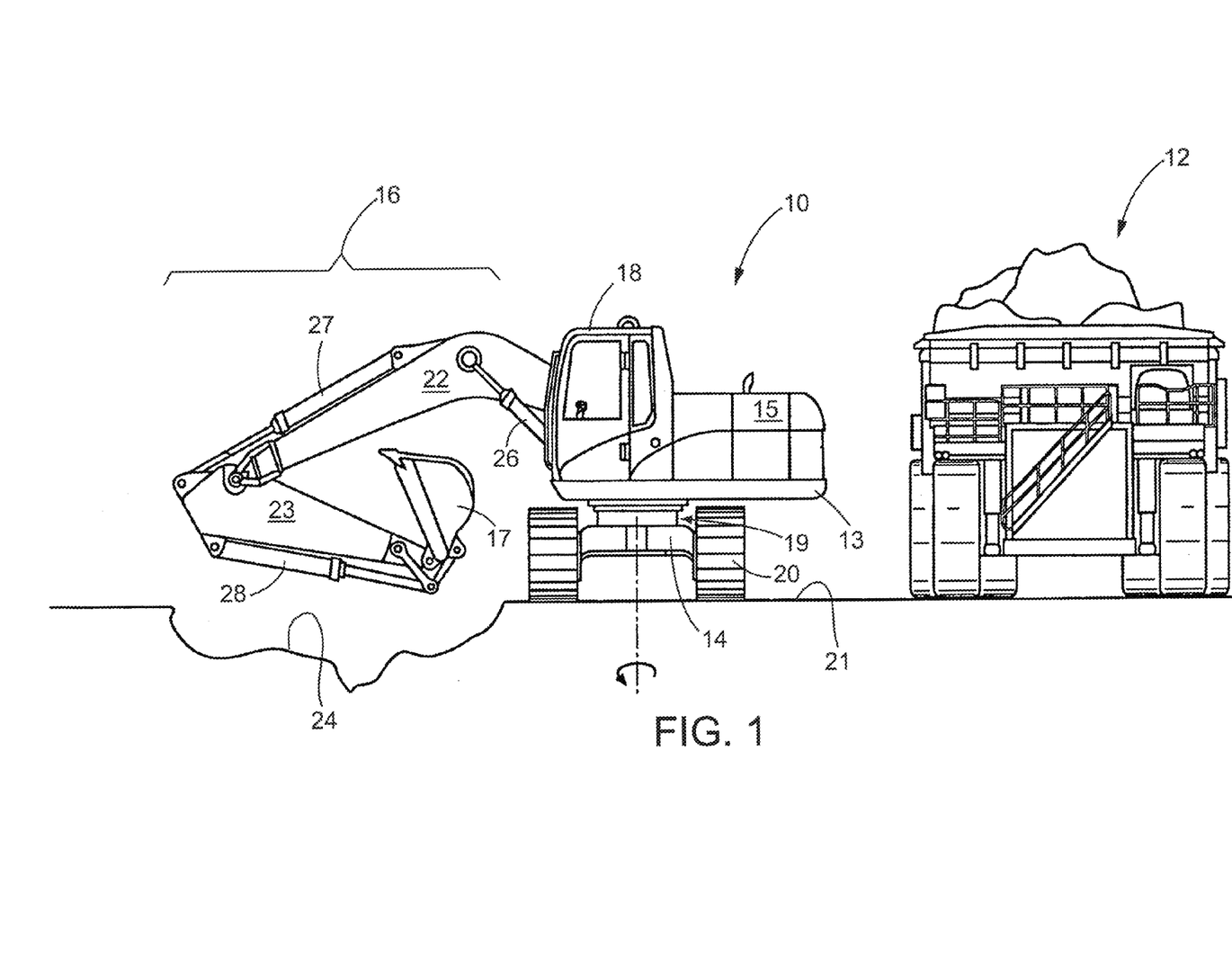
FIG. 1 is a side view of an excavator including a payload cycle detection system in accordance with the disclosure and with an adjacent target vehicle.

FIG. 1 illustrates an exemplary machine 10 such as an excavator having multiple systems and components that cooperate to perform an operation such as excavating earthen material from a dig site 24 and loading it onto a nearby target vehicle such as haul vehicle 12. Machine 10 may include a platform 13, an undercarriage 14, a prime mover 15, and an implement system 16 including a work implement or tool such as bucket 17. Other types of work implements may also be used.

Platform 13 may be rotatably disposed on undercarriage 14 and include an operator station 18 from which an operator may control the operation of machine 10. Rotation of platform 13 relative to undercarriage 14 may be effected by a swing motor 19.

Undercarriage 14 may be a structural support for one or more traction devices 20. Traction devices 20 may include one or more tracks configured to allow translational motion of machine 10 across a work surface 21. Alternatively, traction devices 20 may include wheels, belts, or other traction devices known in the art.

A prime mover 15 may provide power for the operation of machine 10. Prime mover 15 may embody a combustion engine, such as a diesel engine, a gasoline engine, a gaseous fuel powered engine (e.g., a natural gas engine), or any other type of combustion engine known in the art. Prime mover 15 may alternatively embody a non-combustion source of power, such as a fuel cell or a power storage device such as a battery coupled to a motor. Prime mover 15 may provide a rotational output to drive traction devices 20, thereby propelling machine 10. Prime mover 15 may also provide power to other systems and components of machine 10.

Implement system 16 may include one or more linkage members configured to move a load. In one example, the implement system may include a boom member 22 and a stick member 23, and a work implement or tool. A first end of boom member 22 may be pivotally connected to platform 13, and a second end of boom member 22 may be pivotally connected to a first end of stick member 23. The work implement or tool such as bucket 17 may be pivotally connected to a second end of stick member 23.

Each linkage member may include and be operatively connected to one or more actuators such as hydraulic cylinders. More specifically, boom member 22 may be propelled or moved along a path by one or more boom hydraulic cylinders 26 (only one being shown in FIG. 1). Stick member 23 may be propelled by a stick hydraulic cylinder 27. Rotation of the bucket 17 relative to the stick member 23 may be effected by a work implement hydraulic cylinder 28. The linkage members may translate or rotate in a plane that is generally orthogonal to the work surface 21.

Figure 3:
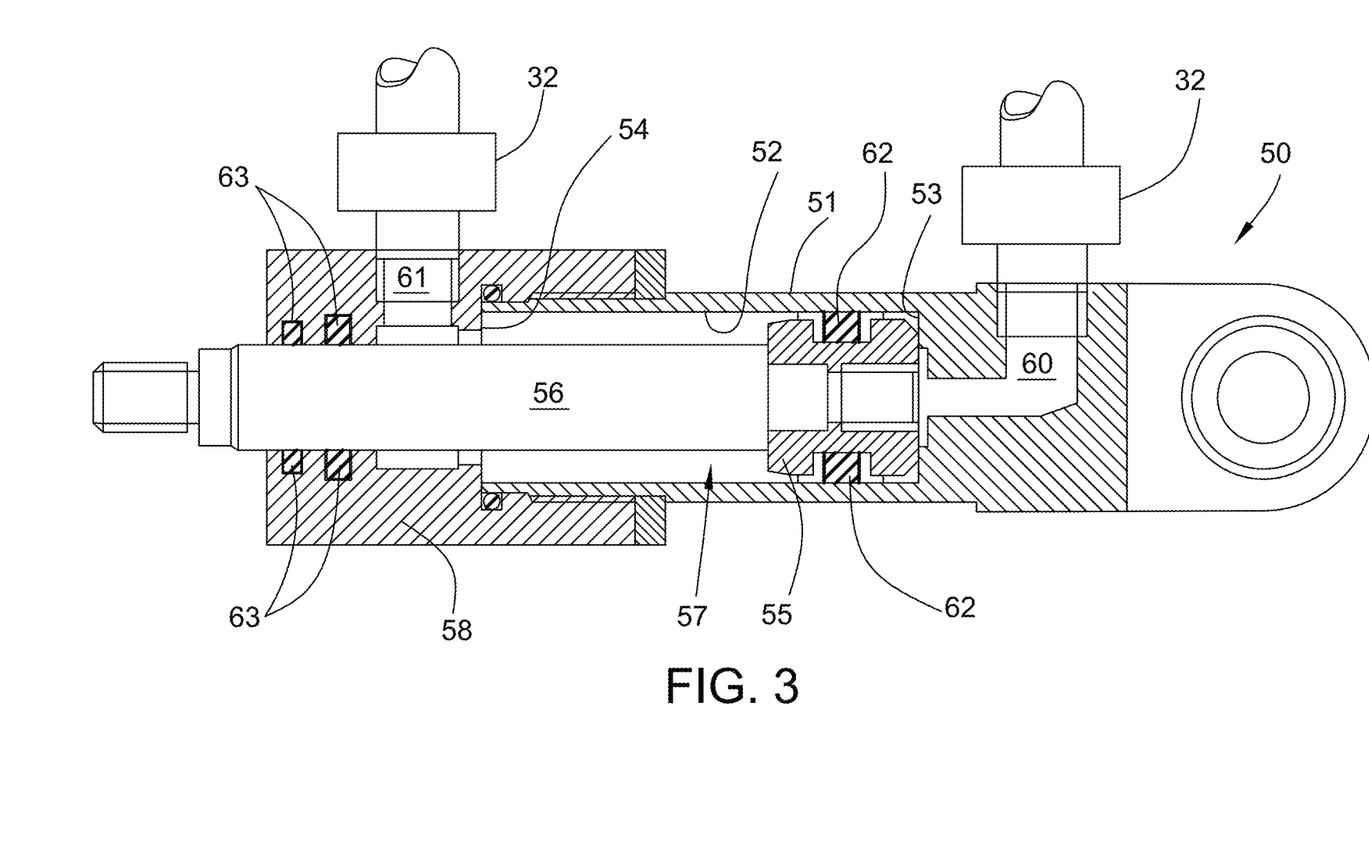
FIG. 3 is a somewhat diagrammatic cross-section of a hydraulic cylinder assembly.

Each of the boom hydraulic cylinders 26, stick hydraulic cylinder 27, and work implement hydraulic cylinder 28 may embody a linear actuator such as the hydraulic cylinder 50 depicted in FIG. 3 having a tubular or cylindrical body 51 and a piston and rod assembly 57 therein arranged to form two distinct pressure chambers. The pressure chambers may be selectively supplied with pressurized fluid and drained of the pressurized fluid to cause the piston and rod assembly 57 to displace within the cylindrical body 51, and thereby change the effective length of the hydraulic cylinders. The flow rate of fluid into and out of the pressure chambers may relate to the speed of extension or retraction of hydraulic cylinders 26, 27, 28, while a pressure differential between the two pressure chambers may relate to the force imparted by the hydraulic cylinders on their associated linkage members. The extension and retraction of the hydraulic cylinders results in the movement of bucket 17. It is also contemplated that the actuators may alternatively embody electric motors, pneumatic motors, or any other actuation devices.

Swing motor 19 may also be driven by differential fluid pressure. Specifically, swing motor 19 may be a rotary actuator including first and second chambers (not shown) located on opposite sides of an impeller (not shown). Upon filling the first chamber with pressurized fluid and draining the second chamber of fluid, the impeller is urged to rotate in a first direction. Conversely, when the first chamber is drained of fluid and the second chamber is filled with pressurized fluid, the impeller is urged to rotate in an opposite direction. The flow rate of fluid into and out of the first and second chambers affects the rotational speed of swing motor 19, while a pressure differential across the impeller affects the output torque thereof.

Machine 10 may be equipped with a plurality of sensors that provide data, directly or indirectly, of the performance or conditions of various aspects of the machine. Angle sensors 30 (FIG. 2) may be located near one or more joints of the linkage members (i.e., the joint between platform 13 and boom member 22, the joint between boom member 22 and stick member 23, the joint between the work implement and stick member 23), and between platform 13 and undercarriage 14. Angle sensors 30 may include rotary encoders, potentiometers, or other angle or sensing devices. In an alternate embodiment, angle sensors 30 may measure the displacement of an actuator and the joint angles may be calculated based upon the position of the actuators and the dimensions of the linkage members. Output signals of angle sensors 30 may be used to determine the state of aspects of machine 10 including implement system 16, such as, for example, the position, the velocity, the acceleration, the angle, the angular velocity, and the angular acceleration of each linkage member, and the angle, the angular velocity, and the angular acceleration of the platform 13 relative to undercarriage 14.

Force sensors 31 may be configured to output a signal usable to determine a force created or experienced by the actuators and/or the linkage members. For example, a force sensor may embody a pressure sensor system including pressure sensors 32 (FIG. 3) located and configured to measure the pressure of the pressurized fluid within or supplied to one or both of the pressure chambers of the boom hydraulic cylinders 26. The measured pressures may be used to determine the force generated by each actuator. The forces together with the physical dimensions of the actuators and linkage members may be used to determine joint torques of the linkage members. Force sensors 31 may alternatively embody strain gauges, piezoelectric transducers, or other force sensing devices located at linkage joints, actuator joints, or any other appropriate location.

Attitude sensor 33 may measure the pitch and roll of machine 10. Attitude sensor 33 may be located at any appropriate location on machine 10, such as, for example, at operator station 18. Attitude sensor 33 may embody one or more gyroscopes, accelerometers, gravitational inclinometers, or any combination thereof.

A control system 35 may be provided to control the operation of the machine 10 including the payload calculation system of the machine. The control system 35, as shown generally in FIG. 2, may include an electronic control module such as controller 36. The controller 36 may receive operator input command signals and control the operation of the various systems of the machine 10. The control system 35 may include one or more operator input devices 34 such as a joystick to control the machine 10 and one or more sensors. The term "sensor" is meant to be used in its broadest sense to include one or more sensors and related components that may be associated with the machine 10 and that may cooperate to sense various functions, operations, and operating characteristics of the machine. The sensors of machine 10 may include a plurality of angle sensors 30, force sensors 31, and attitude sensors 33 (each of which is shown generally in FIG. 2) to provide data and other signals representative of various operating parameters of the machine 10. The controller 36 may communicate with the one or more sensors and the one or more operator input devices 34 via communication lines 38 or wirelessly.

Figure 2:
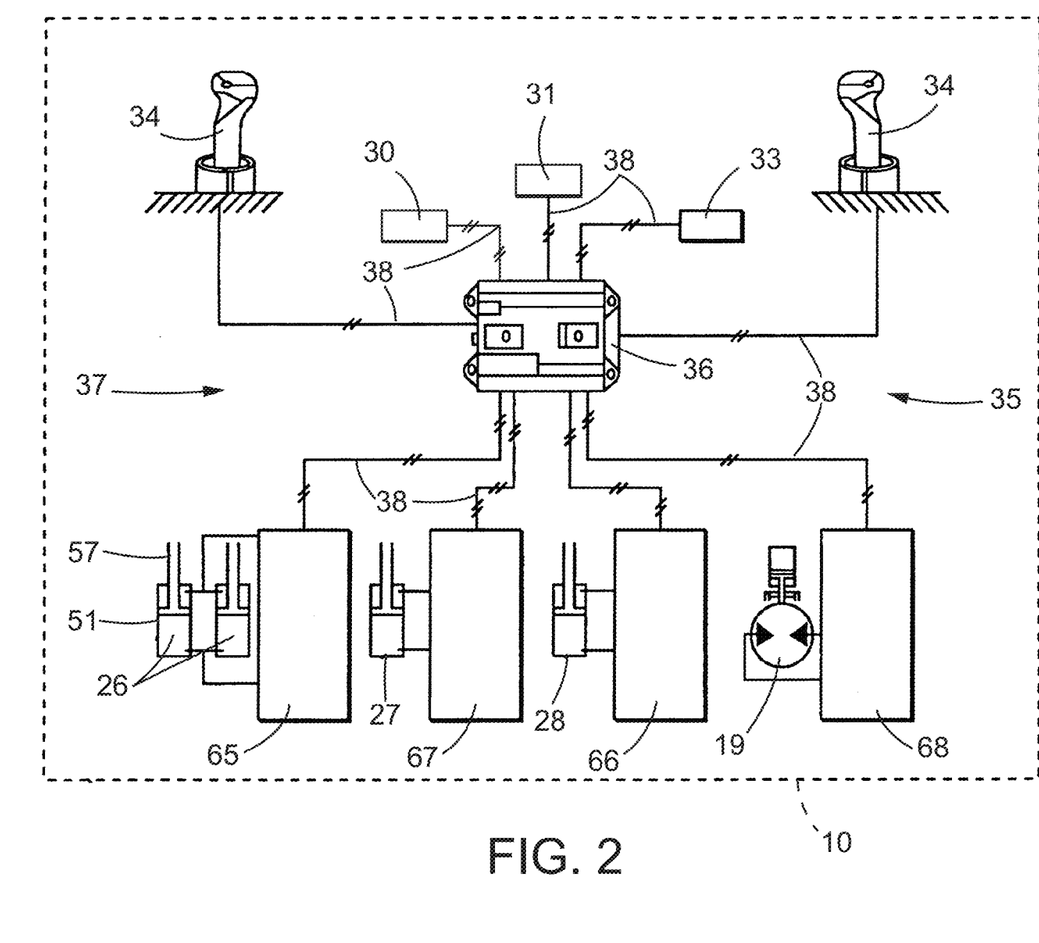
FIG. 2 is a simplified schematic of a control system within the excavator of FIG. 1.

The controller 36 may be an electronic controller that operates in a logical fashion to perform operations, execute control algorithms, store and retrieve data and other desired operations. The controller 36 may include or access memory, secondary storage devices, processors, and any other components for running an application. The memory and secondary storage devices may be in the form of read-only memory (ROM) or random access memory (RAM) or integrated circuitry that is accessible by the controller. Various other circuits may be associated with the controller such as power supply circuitry, signal conditioning circuitry, driver circuitry, and other types of circuitry.

The controller 36 may be a single controller or may include more than one controller disposed to control various functions and/or features of the machine 10. The term "controller" is meant to be used in its broadest sense to include one or more controllers and/or microprocessors that may be associated with the machine 10 and that may cooperate in controlling various functions and operations of the machine. The functionality of the controller 36 may be implemented in hardware and/or software without regard to the functionality. The controller 36 may rely on one or more data maps relating to the operating conditions of the machine 10 that may be stored in the memory of controller. Each of these maps may include a collection of data in the form of tables, graphs, and/or equations. The controller 36 may use the data maps to maximize the performance and efficiency of the machine 10.

The boom hydraulic cylinders 26, the stick hydraulic cylinder 27, the work implement hydraulic cylinder 28, and the swing motor 19 may function together with other cooperating fluid components to move bucket 17 in response to input received from the operator input device 34. In particular, control system 35 may include one or more fluid circuits (not shown) configured to produce and distribute streams of pressurized fluid. A boom control valve 65, a stick control valve 66, a bucket control valve 67, and a swing control valve 68 may be situated to receive the streams of pressurized fluid and selectively meter the fluid to and from the boom hydraulic cylinders 26, the stick hydraulic cylinder 27, the work implement hydraulic cylinder 28, and the swing motor 19, respectively, to regulate the motions thereof.

Controller 36 may be configured to receive input from the operator input device 34 and to command operation of the boom control valve 65, the stick control valve 66, the bucket control valve 67, and the swing control valve 68 in response to the input and based on the data maps described above. Specifically, controller 36 may receive the input device position signal indicative of a desired speed and/or force of bucket 17 in a particular direction, and reference the selected and/or modified data maps stored in the memory of controller 36 to determine flow rate values and/or associated positions for each of the supply and drain elements within the boom control valve 65, the stick control valve 66, the bucket control valve 67, and the swing control valve 68. The flow rates or positions may then be commanded of the appropriate supply and drain elements to cause filling and/or draining of the chambers of the actuators at rates that result in the desired movement of bucket 17.

Referring to FIG. 3, a hydraulic cylinder 50 is depicted. The hydraulic cylinder 50 may include a hollow cylindrical body 51 having a cylindrical cavity 52 with a closed end 53, and an opposite open rod end 54. A cylindrical piston 55 may be fixed to a rod 56 to create a piston and rod assembly 57. The piston and rod assembly 57 is slidably mounted within the cylindrical cavity 52. An end portion 58 may be mounted at the open rod end 54 of the hollow cylindrical body 51 to secure the piston and rod assembly 57 within the hollow cylindrical body.

A piston end oil port 60 may extend through the hollow cylindrical body 51 and establish fluid communication with the cylindrical cavity 52 generally adjacent the closed end 53 of cylindrical cavity 52. A rod end oil port 61 may extend through the hollow cylindrical body 51 and establish fluid communication with the cylindrical cavity 52 generally adjacent the opposite open rod end 54. One or more piston seals 62 may be mounted on the cylindrical piston 55 and interact with the hollow cylindrical body 51 to form a seal between the piston 55 and the hollow cylindrical body 51. One or more rod end hydraulic seals or rod seals 63 may be mounted on the end portion 58 and interact with the rod 56 to form a seal between the rod 56 and the end portion 58.

By supplying pressurized fluid to one of the oil ports and draining fluid from the other oil port, the piston and rod assembly 57 may be driven in one of two directions within the hollow cylindrical body 51. Motion of the piston and rod assembly 57 in one direction extends the rod 56 from the hollow cylindrical body 51, while the motion in the opposite direction retracts the rod into the hollow cylindrical body.

The force exerted by the hydraulic cylinder 50 is generally equal to the input force such as from a pressurized fluid less the friction and other losses associated with the hydraulic cylinder. In one embodiment, the input force supplied by the pressurized hydraulic fluid may be determined from the hydraulic pressure sensed by a cylinder force sensor such as the pressure sensors 32 on or associated with the hydraulic cylinder 50. More specifically, a pressure sensor system 37 (FIG. 2) may be configured to provide a piston end cylinder pressure signal indicative of a piston end cylinder pressure of the hydraulic cylinder 50 and a rod end cylinder pressure signal indicative of a rod end cylinder pressure of the hydraulic cylinder 50. The controller may be configured to determine a piston seal coefficient of friction and a rod hydraulic seal coefficient of friction. The controller 36 may utilize a force signal received from the sensors indicative of the pressure at each end of the cylindrical cavity 52 as well as the dimensions of the cylindrical piston 55 and the rod 56 to determine the force exerted by the hydraulic fluid within the hydraulic cylinder 50.

The friction associated with the hydraulic cylinder 50 is generally composed of three components, namely Coulomb friction, viscous friction, and hydraulic pressure induced seal friction. Coulomb friction generally represents friction associated with mechanical surfaces rubbing together and is generally constant. Viscous friction generally represents the force required to push hydraulic fluid through restrictive passages associated with the hydraulic cylinder 50 and is generally a function of the velocity of the piston 55 of the hydraulic cylinder 50. Seal friction generally represents the friction of the seals between the components of the hydraulic cylinder 50.

The friction force ($F_{Fric}$) associated with hydraulic cylinder 50 may be generally represented by the equation:

$$F_{Fric} = c_1 |P_{RE} - P_{ambient}| + c_2 |P_{HE} - P_{RE}| + c_3 |v_{cyl}| + c_0 \quad (1)$$

where $c_1$ is the coefficient of friction of the rod seal 63 and $c_2$ is the coefficient of friction of the piston seal 62, $P_{RE}$ is the hydraulic pressure measured at the rod end oil port 61, $P_{ambient}$ is the ambient pressure of the operating environment, $P_{HE}$ is the hydraulic pressure measured at the piston end oil port 60, $c_3$ is the viscous friction coefficient, $c_0$ is the Coulomb friction coefficient, and $v_{cyl}$ is the velocity of the piston and rod assembly 57. It should be noted that the viscous friction coefficient ($c_3$) and the Coulomb friction coefficient ($c_0$) may include additional frictional forces associated with the hydraulic cylinder 50. In the case of boom hydraulic cylinder 26, such additional frictional forces may include any forces associated with moving the boom member 22 such as friction at the mounting pins used to mount the boom hydraulic cylinder as well as friction at the joint between the platform 13 and the boom member 22.

Figure 4:
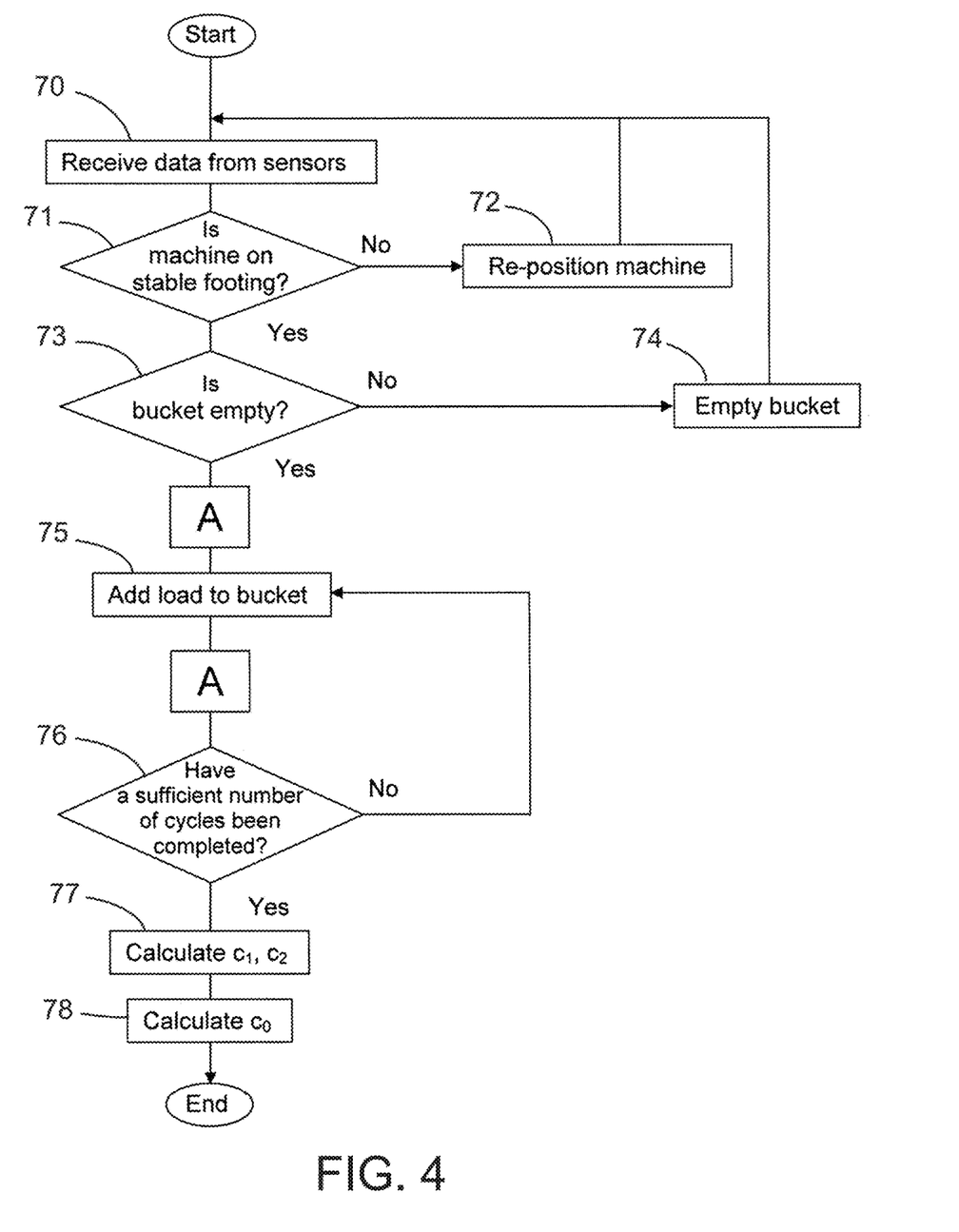
FIG. 4 is a flowchart illustrating a process for determining the coefficients of friction for the seals of a hydraulic cylinder in accordance with the disclosure.
Figure 5:
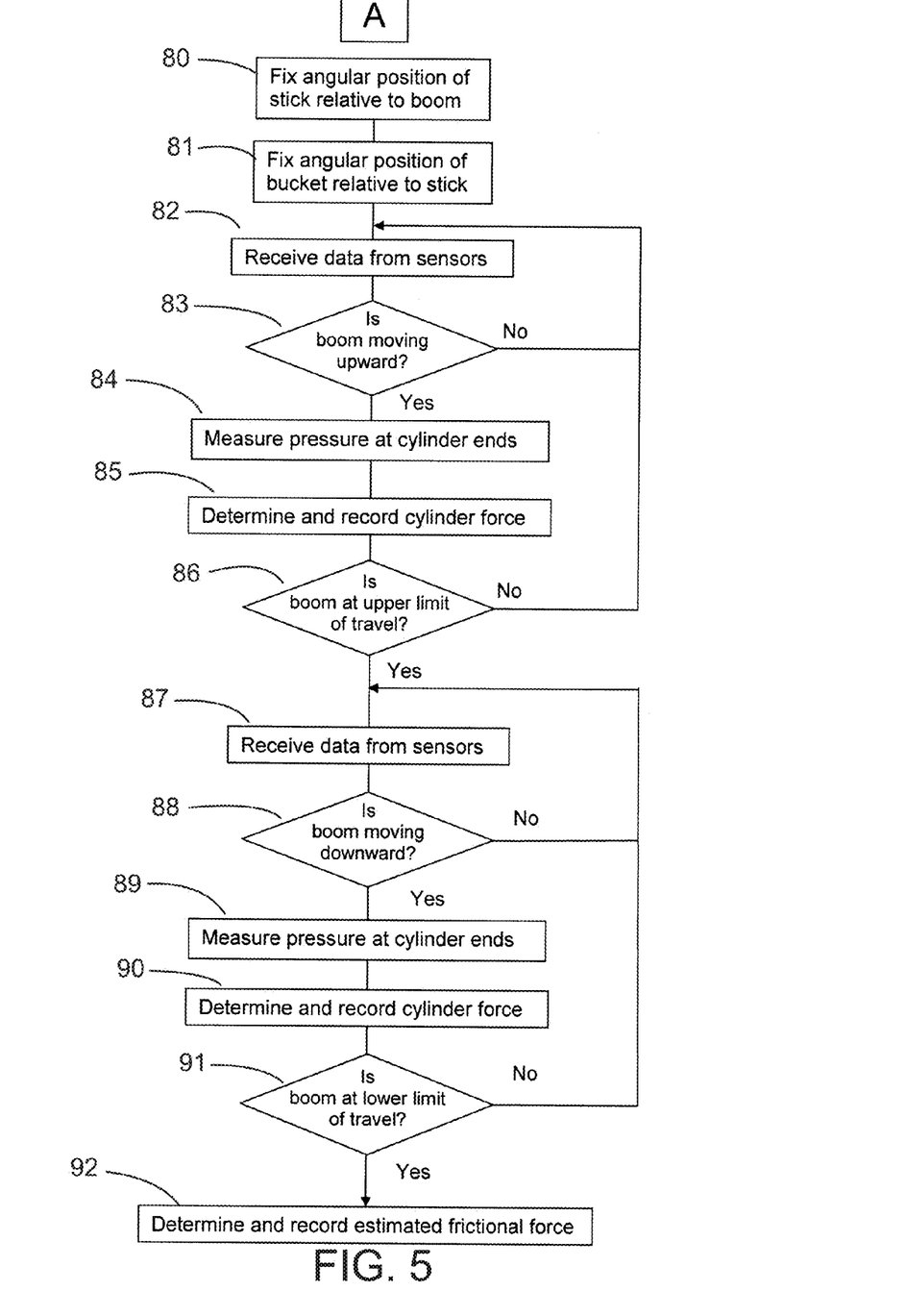
FIG. 5 is a flowchart illustrating a further aspect of the process of FIG. 4.

In some situations, the viscous friction coefficient ($c_3$) and the Coulomb friction coefficient ($c_0$) may be readily estimated but the coefficients of friction ($c_1$, $c_2$) of the seals are generally more difficult to estimate. The control system 35 may include a system for determining the coefficients of friction ($c_1$, $c_2$) of the seals of the hydraulic cylinder 50. FIGS. 4-5 depict flowcharts of a process for estimating such coefficients of friction ($c_1$, $c_2$) of the seals of the hydraulic cylinder 50. At stage 70, the controller 36 receives data from various sensors that may be used to determine the state of the machine 10 including implement system 16. More specifically, the controller 36 may receive data from the various angle sensors 30 associated with each of the joints of the linkage members as well as data from the attitude sensor 33 that provides data indicative of the pitch and roll of machine 10. Still further, the controller 36 may also receive data from the force sensors 31 that may be used to determine the force created or experienced by the actuators and/or the linkage members. These force sensors 31 may include a pressure sensor 32 associated with each of the piston end oil port 60 and the rod end oil port 61 to determine the pressure of the hydraulic fluid at the respective ports.

At decision stage 71, the controller 36 may determine whether the machine 10 is on stable footing. The controller 36 may receive signals from the attitude sensor 33 and determine the angular pitch and roll as well as the angular rate and the angular acceleration of each to determine whether the machine 10 is rocking or whether the machine is sufficiently stable to determine the coefficients of friction of the seals. If the machine 10 is not sufficiently stable, the controller 36 may instruct the operator to re-position the machine at stage 72.

At decision stage 73, the controller may determine whether the bucket 17 is empty. The controller 36 may utilize a payload estimation system (not shown) to determine whether the bucket 17 is empty or the controller may instruct the operator to empty the bucket at stage 74. In some situations, it may be desirable to determine the coefficients of seal friction without starting with an empty bucket 17. Once the bucket 17 is empty at decision stage 73, or a decision has been made not to empty the bucket, the process "A" of FIG. 5 for determining the frictional force associated with the boom hydraulic cylinder 26 may be followed.

At stage 80, the controller 36 may fix the angular position of a second linkage member such as the stick member 23 relative to the boom member 22. At stage 81, the angular position of the bucket 17 may be fixed relative to the stick member 23. At stage 82, the controller continues to receive data from the various sensors as described above with respect to stage 70.

At decision stage 83, the controller 36 determines whether the boom member 22 is moving upward in a desired manner. It may be desirable to move the boom member 22 upward at a relatively slow and relatively constant velocity to generally reduce or eliminate the impact of the viscous friction component ($c_3 |v_{cyl}|$) from equation (1) above. Such movement of the boom member 22 may be achieved by moving the piston 55 at a relatively slow and generally constant rate. In one example, it may be desirable to move the boom member 22 upward at a predetermined rate no greater than approximately one degree per second. In another example, it may be desirable to move the boom member 22 upward at a predetermined rate no greater than approximately two degrees per second. Other rates may be utilized, if desired. It should be noted that moving the boom member 22 too slowly may result in stopping of the boom hydraulic cylinder 26 or other components of implement system 16 which may result in decreased accuracy due to the affect of static friction.

If the boom member 22 is not moving upward in a desired manner at decision stage 83, the controller 36 may not utilize data received from the various sensors for the calculation of the friction coefficients and the controller may continue to receive sensor data at stage 82. If the boom member 22 is moving upward in a desired manner at decision stage 83, the controller 36 may receive at stage 84 signals indicative of the pressure at the boom hydraulic cylinders 26. More specifically, the controller 36 may receive a piston end cylinder pressure signal indicative of a piston end cylinder pressure at piston end oil port 60 ($P_{HE}$) of each boom hydraulic cylinder 26. In addition, the controller may receive a rod end cylinder pressure signal indicative of a rod end cylinder pressure at the rod end oil port 61 ($P_{RE}$) of each boom hydraulic cylinder 26.

At stage 85, the controller 36 may utilize the piston end cylinder pressure and the rod end cylinder pressure of each boom hydraulic cylinder 26 as well as the dimensions of the cylindrical piston 55 and the rod 56 of each boom hydraulic cylinder to determine the force exerted by the hydraulic fluid within each boom hydraulic cylinder 26. This force may be recorded by the controller 36 as a function of the angle of the boom member 22 relative to the platform 13.

Figure 6:
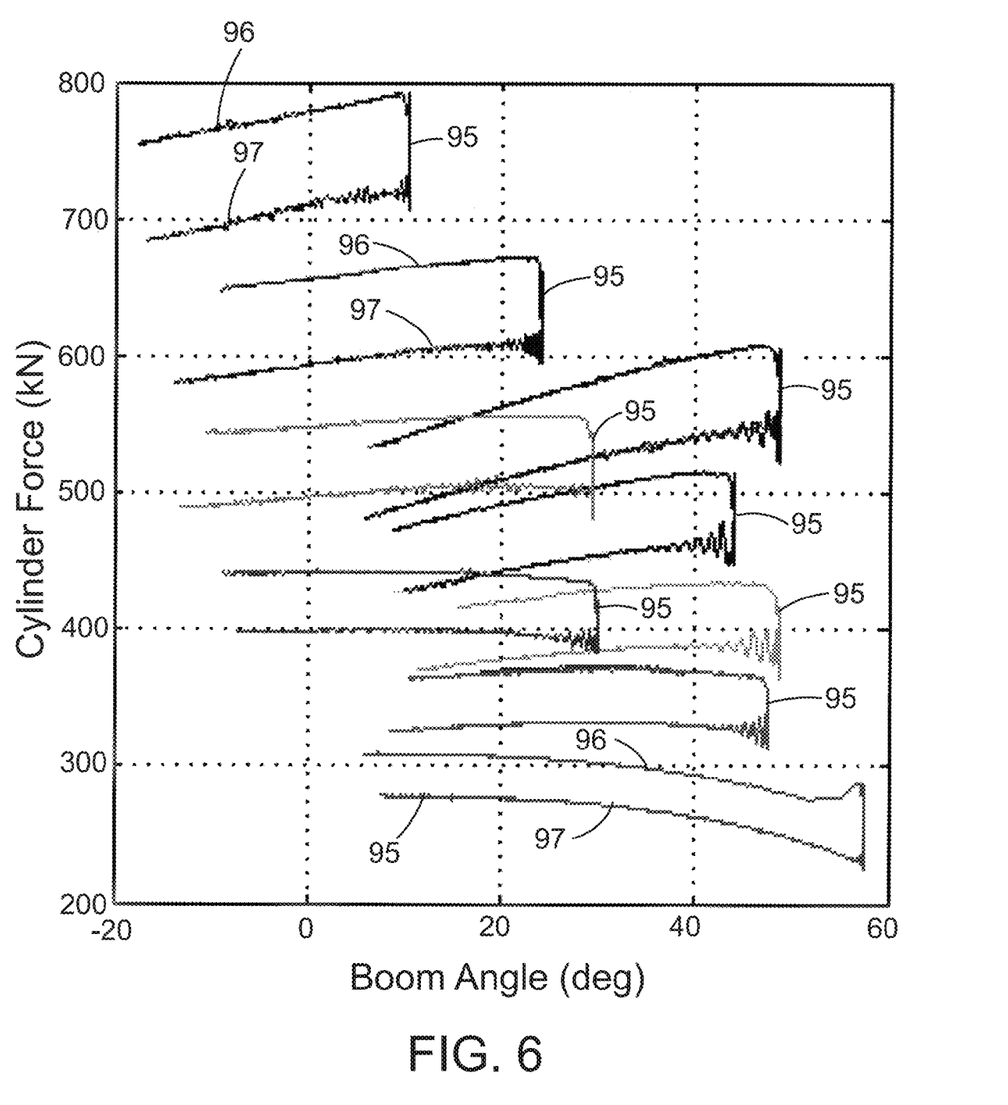
FIG. 6 is an exemplary performance graph of the force at the boom hydraulic cylinder as a function of boom angle for a plurality of payloads.

At decision stage 86, the controller 36 may determine whether the boom member 22 is at an upper limit of movement relative to the platform 13. If the boom member 22 is not at the upper limit of movement at decision stage 86, the controller 36 continues to receive sensor data at stage 82 and the process of determining whether the boom is moving upward at decision stage 83, measuring the pressures at the boom hydraulic cylinders 26 at stage 84, and determining and recording the cylinder force at stage 85 are repeated. It should be noted that the upper limit of movement of the boom member 22 (and thus the path the boom member travels) may change depending upon the payload within the bucket 17. For example, as shown in FIG. 6, the sets 95 of data points reflect different ranges of movement of the boom member 22 relative to platform 13.

Once the boom is at its upper limit of travel at decision stage 86, the controller 36 continues to receive data at stage 87 from the sensors as described above with respect to stage 70. At decision stage 88, the controller 36 determines whether the boom member 22 is moving downward in a desired manner. It may be desirable to move the boom member 22 downward at a relatively slow and relatively constant velocity as described above with respect to decision stage 83. By moving the boom downward at a relatively slow rate, the impact of the viscous friction and thus the viscous friction component $(c_3 |v_{cyl}|)$ of equation (1) above is generally reduced or eliminated. In one example, it may be desirable to move the boom member 22 downward at a predetermined rate no greater than approximately one degree per second. In another example, it may be desirable to move the boom member 22 downward at a predetermined rate no greater than approximately two degrees per second. Other rates may be utilized, if desired. As stated above, moving the boom member 22 too slowly may result in decreased accuracy due to the affect of static friction.

If the boom member 22 is not moving downward in a desired manner at decision stage 88, the controller 36 may not utilize data received from the various sensors for the calculation of the friction coefficients and the controller may continue to receive data at stage 87. If the boom member 22 is moving downward in a desired manner at decision stage 88, the controller 36 may receive at stage 89 signals indicative of the pressure at the boom hydraulic cylinders 26. More specifically, the controller 36 may receive a piston end cylinder pressure signal indicative of a piston end cylinder pressure at piston end oil port 60 of each boom hydraulic cylinder 26. In addition, the controller 36 may receive a rod end cylinder pressure signal indicative of a rod end cylinder pressure at the rod end oil port 61 of each boom hydraulic cylinder 26.

At stage 90, the controller 36 may utilize the piston end cylinder pressure and the rod end cylinder pressure of each boom hydraulic cylinder 26 as well as the dimensions of the cylindrical piston 55 and the rod 56 of each boom hydraulic cylinder to determine the force exerted by the hydraulic fluid within each boom hydraulic cylinder 26. This force may be recorded by the controller 36 as a function of the angle of the boom member 22 relative to the platform 13.

At decision stage 91, the controller 36 may determine whether the boom member 22 is at a lower limit of movement relative to the platform 13. If the boom member 22 is not at the lower limit of movement at decision stage 91, the controller 36 may continue to receive sensor data at stage 87 and the process of determining whether the boom member 22 is moving downward at decision stage 88, measuring the pressure of the boom hydraulic cylinders 26 at stage 89, and determining and recording the cylinder forces at stage 90 are repeated. As with the upper limit of movement described above, the lower limit of movement of the boom member 22 may change depending upon the load within the bucket 17.

Once the boom member 22 is at its lower limit of travel at decision stage 91, the controller 36 may determine at stage 92 an estimate of the frictional force of each of the boom hydraulic cylinders 26. By moving the boom member 22 relatively slowly (e.g., less than approximately 2° per second), the determination of the force at the boom hydraulic cylinder 26 may be simplified to the following equation:

$$F = F_{gravity} + F_{Fric} \qquad (2)$$

where F equals the force on the boom hydraulic cylinder 26, $F_{gravity}$ is the gravitational force acting on the boom hydraulic cylinder and is a function of the mass being lifted by the boom hydraulic cylinder, gravitational acceleration, and the angle of the boom member 22 with respect to gravity, and $F_{Fric}$ is the frictional force associated with the boom hydraulic cylinder and always opposes the movement of the cylinder.

As the boom member 22 is moved upward at a constant velocity, the force $(F_{lift})$ required to lift the boom member 22 is the gravitational force plus the frictional force associated with the boom hydraulic cylinder 26 and may be approximated as:

$$F_{lift} = F_{gravity} + F_{Fric} \qquad (3)$$

Similarly, the force $(F_{lower})$ required to lower the boom member 22 is the gravitational force minus the frictional force associated with the boom hydraulic cylinder 26 and may be approximated as:

$$F_{lower} = F_{gravity} + F_{fric} \qquad (4)$$

As a result, the difference between the force required to lift the boom member 22 and the force required to lower the boom member 22 at each boom linkage angle may be stated as:

$$F_{lift} - F_{lower} = (F_{gravity} + F_{fric}) - (F_{gravity} - F_{fric}) \qquad (5)$$

which simplifies to:

$$F_{lift} - F_{lower} = 2F_{fric} \qquad (6)$$

Thus, the difference at a particular angle of the boom member 22 between the force $(F_{lift})$ of the boom hydraulic cylinder 26 required to lift the boom member 22 and the force $(F_{lower})$ required to lower the boom member is twice the frictional force $(F_{fric})$ associated with the boom hydraulic cylinder.

Upon the completion of the frictional force determination process "A" of FIG. 5, a load may be added to bucket 17 at stage 75. It is not necessary to add a load of a specific amount but rather change the load within the bucket 17 to create additional data for use by the controller 36. The frictional force determination process "A" may then be repeated to generate additional data of estimated frictional forces of each boom hydraulic cylinder 26 with the increased load in the bucket 17. At decision stage 76, the controller 36 may determine whether a sufficient number of cycles of the frictional force determination process "A" have been completed so that the controller 36 may determine the coefficient of friction $(c_1)$ of the rod seal 63 (i.e., the piston end hydraulic seal coefficient of friction) and the coefficient of friction $(c_2)$ of the piston seal 62 (i.e., the rod end hydraulic seal coefficient of friction). If a sufficient number of cycles have not been completed, the operator may be instructed at stage 75 to add an additional load to the bucket 17 and repeat the frictional force determination process "A." Once a sufficient number of cycles of the frictional force determination process "A" have been completed at decision stage 76, the controller 36 may determine at stage 77 the coefficient of friction $(c_1)$ of the rod seal 63 and the coefficient of friction $(c_2)$ of the piston seal 62 based upon the estimated frictional forces of the boom hydraulic cylinder 26.

Figure 7:
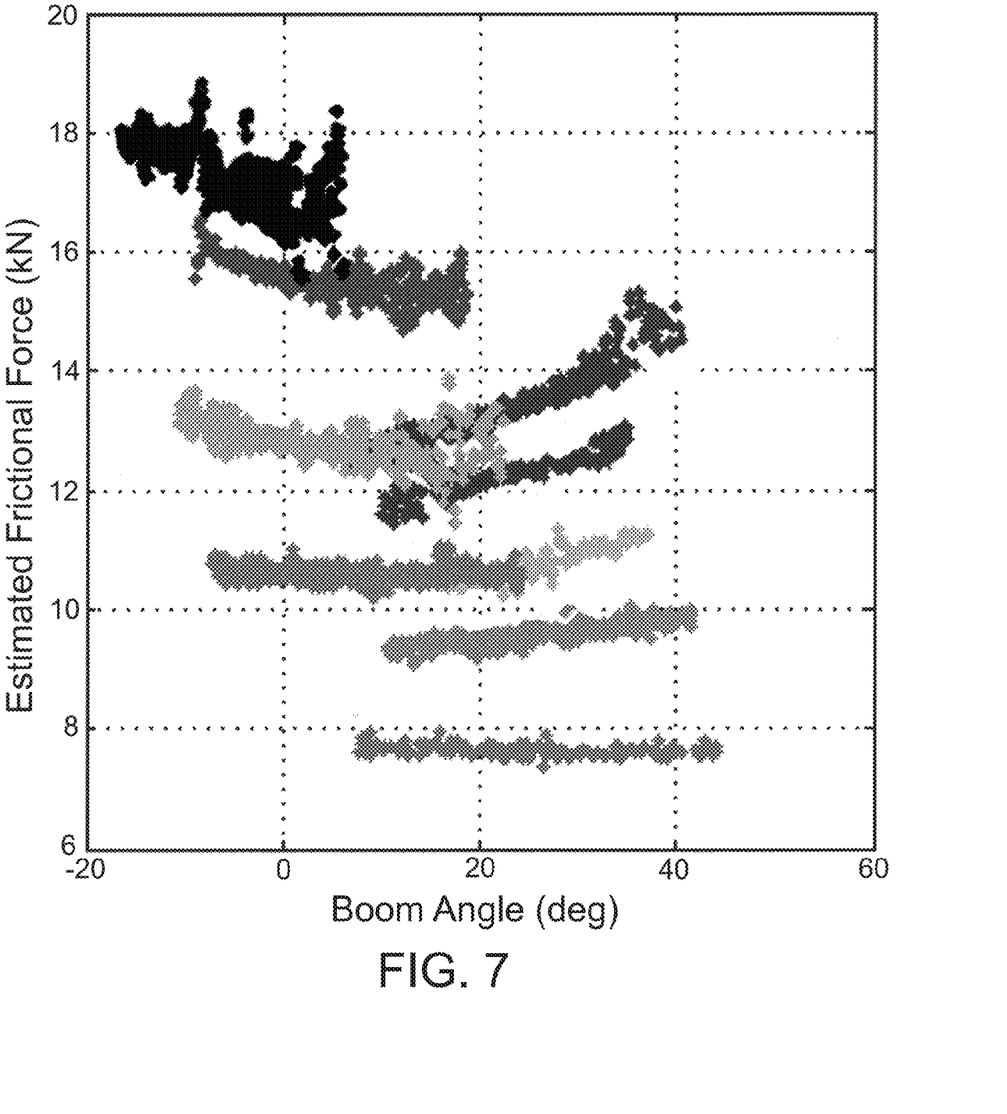
FIG. 7 is an exemplary performance graph of estimated frictional forces associated with the boom hydraulic cylinder as a function of boom angle for the plurality of payloads depicted in FIG. 6.
Figure 8:
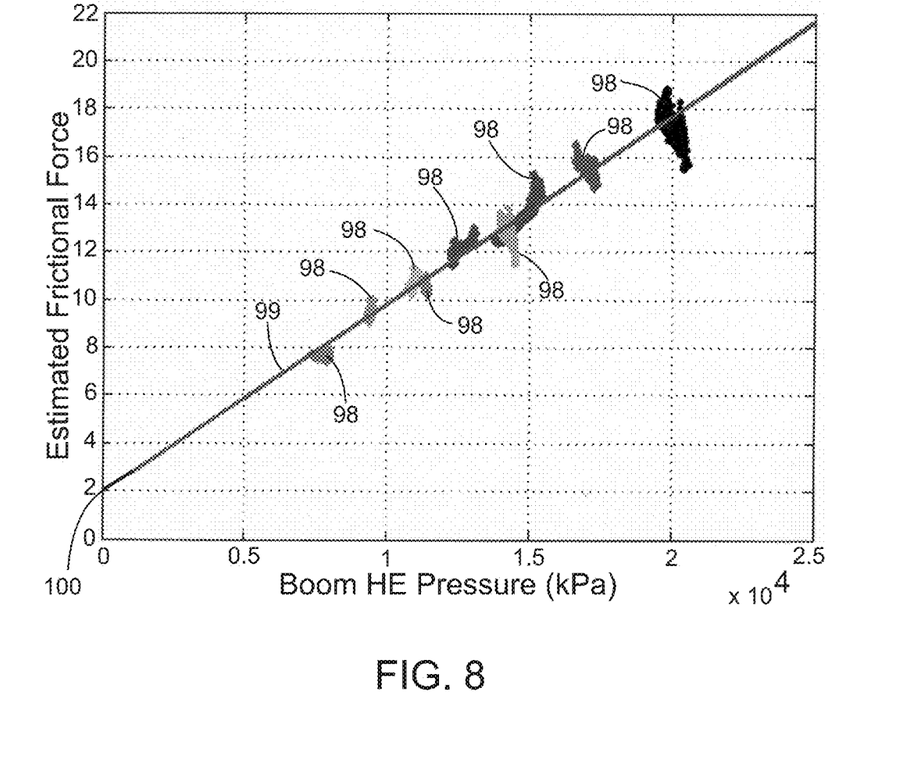
FIG. 8 is an exemplary performance graph of the estimated frictional force associated with the boom hydraulic cylinder as a function of the pressure of the boom hydraulic cylinder at the piston end oil port for the plurality of payloads depicted in FIGS. 6-7.

The determination of the coefficient of friction $(c_1)$ of the rod seal 63 and the coefficient of friction $(c_2)$ of the piston seal 62 may be further understood by referring to FIGS. 6-8. FIG.

6 depicts a plot showing a plurality of sets 95 of data points generated during a plurality of passes through the process stages 82-91. Each set 95 of data points depicts the cylinder force for a particular load within the bucket 17 with respect to the angle of the boom member 22 relative to the platform 13.

As stated above, the upper and lower limits of travel of the boom member 22 may change depending on the load within the bucket 17. As depicted in FIGS. 6-7, many of the sets 95 of data points begin and end at different boom angles relative to the platform 13. From FIGS. 6-7 it may be seen that the path along which the boom member 22 is moved may be a different length for each load. The boom member 22 may move along a first path length for a first load and along a second path length for a second load. In one embodiment, the first and second path lengths may be different. In another embodiment, the first and second path lengths may be the same.

The force on the boom hydraulic cylinder 26 will generally increase as the load within the bucket 17 increases. Accordingly, the plurality of sets 95 of data points correspond to the cylinder force with different loads within the bucket 17. The cylinder force for each load may be determined based at least in part upon the pressure at the piston end oil port 60 and the rod end oil port 61 of each boom hydraulic cylinder 26 as well as the dimensions of the cylindrical piston 55 and the rod 56 of each boom hydraulic cylinder 26. The upper line 96 of each set 95 of data points depicts the cylinder force as the boom member 22 is moved upward during process stages 82-86 and the lower line 97 depicts the cylinder force as the boom member 22 is moved downward during process stages 87-91.

In other words, the upper line 96 of each set 95 of data points is the force ($F_{lift}$) at the boom hydraulic cylinder 26 required to lift the boom member 22 and the lower line 97 of each set 95 of data points is the force ($F_{lower}$) at the boom hydraulic cylinder 26 required to lower the boom member. The difference between the upper line 96 and the lower line 97 of each set 95 of data points is twice the force due to the friction of moving the boom member 22. Thus, the estimated frictional force ($F_{fric}$) is equal to one half of the difference between the upper line 96 and the lower line 97 of each set 95 of data points.

FIG. 7 depicts a plot of a plurality of sets 98 of data points of the estimated frictional force ($F_{fric}$) associated with the boom hydraulic cylinder 26 for a particular load within the bucket 17 with respect to the angle of the boom member 22 relative to the platform 13. In other words, FIG. 7 depicts one half the difference between the upper line 96 and the lower line 97 of each set 95 of the data points of FIG. 6. In performing such a calculation, each data point along the lower line 97 is subtracted from a data point along the upper line 96 that corresponds to the same boom angle.

To calculate at stage 77 the coefficient of friction ($c_1$) of the rod seal 63 and the coefficient of friction ($c_2$) of the piston seal 62, the controller 36 may utilize the sets 98 of estimated frictional forces depicted in FIG. 7. In one example, the controller 36 may plot the estimated frictional forces depicted in FIG. 7 versus the hydraulic pressure measured at the piston end oil port 60 ($P_{HE}$) and the hydraulic pressure measured at the rod end oil port 61 ($P_{RE}$). In doing so, the controller 36 may create a three-dimensional graph depicting the frictional force associated with the boom hydraulic cylinder 26 as it varies with both the hydraulic pressure measured at the piston end oil port 60 ($P_{HE}$) and the hydraulic pressure measured at the rod end oil port 61 ($P_{RE}$). Noting that the viscous friction component ($c_3|v_{cyl}|$) of equation (1) above is a function of the velocity of the piston 55, and that the boom member 22 was moved relatively slowly during the frictional force determination process "A," the viscous friction component ($c_3|v_{cyl}|$) of the equation (1) may be set to zero to simplify the equation. Accordingly, the equation for the friction force ($F_{Fric}$) moving at slow speeds may be approximated by the equation:

$$F_{Fric} = c_1|P_{RE} - P_{ambient}| + c_2|P_{HE} - P_{RE}| + c_0 \quad (7)$$

The three-dimensional graph may be used to determine the coefficient of friction ($c_1$) of the rod seal 63 and the coefficient of friction ($c_2$) of the piston seal 62 by using a curve fit procedure.

For purposes of illustration, FIG. 8 depicts a two-dimensional graph of the estimated frictional forces associated with the boom hydraulic cylinder 26 of FIG. 7 versus the hydraulic pressure measured at the piston end oil port 60 ($P_{HE}$). (In many circumstances, the hydraulic pressure measured at the piston end oil port 60 ($P_{HE}$) may be substantially greater than the hydraulic pressure measured at the rod end oil port 61 ($P_{RE}$). As a result, the graph of FIG. 8 may generally approximate the slope of the three-dimensional graph developed by the controller 36.) A straight line 99 drawn through the frictional force data depicts the generally linear manner in which the estimated frictional force associated with the boom hydraulic cylinder 26 may vary with the hydraulic pressure measured at the piston end oil port 60 ($P_{HE}$).

If desired, the coefficient of Coulomb friction ($c_0$) may be determined at stage 78 by extending the line 99 until the piston end hydraulic pressure ($P_{HE}$) and the rod end hydraulic pressure ($P_{RE}$) are both zero at the intersection 100 with the vertical axis. As depicted in FIG. 8, the piston end hydraulic pressure ($P_{HE}$) is zero at intersection 100. In the alternative, the coefficient of Coulomb friction ($c_0$) may be estimated as it is generally constant or it may be included as part of other estimated parameters within the control system 35. Similarly, the coefficient of viscous friction ($c_3$) in equation (1) may be calculated using an additional calibration procedure after determining the coefficient of friction ($c_1$) of the rod seal 63, the coefficient of friction ($c_2$) of the piston seal 62, and the coefficient of Coulomb friction ($c_0$), or may be aggregated with other estimated parameters within the control system 35.

To reiterated and in summary, the bucket 17 is moved in a desired manner with a first load and then the procedure is repeated with one or more additional loads and the controller 36 may determine the coefficient of friction ($c_1$) of the rod seal 63 and the coefficient of friction ($c_2$) of the piston seal 62. More specifically, between stages 82-86, the controller 36 receives signals as the bucket 17 engages a first load (which may be zero) and the bucket is moved in a first direction (e.g., upward). Since the force signals are based upon the bucket 17 moving a first load in a first direction, the plurality of force signals received by the controller during this movement may be designated or characterized as a plurality of first load first direction force signals.

Between stages 87-91, the controller 36 receives signals as the bucket 17 engages the first load and the bucket is moved in a second direction generally opposite the first direction (e.g., downward). Since the force signals are based upon the bucket 17 moving the first load in a second direction, the plurality of force signals received by the controller during this movement may be designated or characterized as a plurality of first load second direction force signals. The controller 36 may determine at stage 92 a first friction force based at least in part upon a difference between the first load first direction force signals and the first load second direction force signals.

A second load may be added to the bucket 17 at stage 75 and the process of stages 82-86 repeated with the controller 36 receiving a plurality of second load first direction force signals and the process of stages 87-91 repeated with the controller 36 receiving a plurality of second load second direction force signals. The controller 36 may determine at stage 92 a second friction force based at least in part upon a difference between the second load first direction force signals and the second load second direction force signals.

If desired, a third load may be added to the bucket 17 at stage 75 and the process of stages 82-86 repeated with the controller 36 receiving a plurality of third load first direction force signals and the process of stages 87-91 repeated with the controller 36 receiving a plurality of third load second direction force signals. The controller 36 may determine at stage 92 a third friction force based at least in part upon a difference between the third load first direction force signals and the third load second direction force signals. This process may be repeated a desired number of times with different loads until a sufficient number of cycles have been completed at stage 76. At such time, a sufficient number of data points will be recorded comparing estimated friction forces versus pressure at the hydraulic cylinder 50. The controller 36 may then determine at stage 77 the coefficient of friction $c_1$ of the rod seal 63 and the coefficient of friction $c_2$ of the piston seal 62 by using a curve fit procedure. If desired, the controller 36 may also determine the coefficient of Coulomb friction ($c_0$) at stage 78.

INDUSTRIAL APPLICABILITY

The industrial applicability of the system for determining coefficients of seal friction described herein will be readily appreciated from the foregoing discussion. The foregoing discussion is applicable to systems including hydraulic actuators such as hydraulic cylinders 50 in which it is desirable to accurately determine the friction within a hydraulic cylinder. The disclosed system permits the determination of the coefficients of friction of the seals within a hydraulic cylinder as a function of the pressure or force of the hydraulic cylinder. As a result, the system may increase the accuracy of a system that utilizes the force of the cylinder as part of its operation.

In one example, a payload estimation system may use the force experienced by one or more hydraulic cylinders 50 to determine or estimate the payload on a work implement or tool. Since the friction due to the piston seal 62 and the rod seal 63 are a function of the pressure at the hydraulic cylinder 50, determining the coefficients of friction for the seals may permit an increase in accuracy of the payload estimation process. Other systems that are also dependent on force reading from hydraulic cylinders may also benefit from the increased accuracy gained by determining the coefficients of friction for the seals.

It will be appreciated that the foregoing description provides examples of the disclosed system and technique. However, it is contemplated that other implementations of the disclosure may differ in detail from the foregoing examples. All references to the disclosure or examples thereof are intended to reference the particular example being discussed at that point and are not intended to imply any limitation as to the scope of the disclosure more generally. All language of distinction and disparagement with respect to certain features is intended to indicate a lack of preference for those features, but not to exclude such from the scope of the disclosure entirely unless otherwise indicated.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context.

Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

The invention claimed is:

1. A system for determining a hydraulic seal coefficient of friction of a hydraulic cylinder assembly, comprising:
   a linkage member for moving a load, the linkage member being movable along a path;
   a hydraulic cylinder assembly operatively connected to the linkage member for moving the linkage member along the path;
   a force sensor configured to provide a force signal indicative of a force of the hydraulic cylinder assembly, the force sensor including a pressure sensor system configured to provide a piston end cylinder pressure signal indicative of a piston end cylinder pressure of the hydraulic cylinder assembly and a rod end cylinder pressure signal indicative of a rod end cylinder pressure of the hydraulic cylinder assembly; and
   a controller configured to:
      receive a plurality of first load first direction force signals as the hydraulic cylinder assembly moves the linkage member along the path in a first direction and the linkage member engages a first load;
      receive a plurality of first load second direction force signals as the hydraulic cylinder assembly moves the linkage member along the path in a second direction and the linkage member engages the first load, the second direction being generally opposite the first direction;
      determine a first friction force based at least in part upon a difference between the plurality of first load first direction force signals and the plurality of first load second direction force signals;
      receive a plurality of second load first direction force signals as the hydraulic cylinder assembly moves the linkage member along the path in the first direction and the linkage member engages a second load;
      receive a plurality of second load second direction force signals as the hydraulic cylinder assembly moves the linkage member along the path in the second direction and the linkage member engages the second load;
      determine a second friction force based at least in part upon a difference between the plurality of second load first direction force signals and the plurality of second load second direction force signals; and
      determine a piston end hydraulic seal coefficient of friction and a rod end hydraulic seal coefficient of friction based at least in part upon the first friction force and the second friction force.

2. The system of claim 1, wherein the controller is further configured to determine a coefficient of Coulomb friction associated with the hydraulic cylinder assembly based at least in part upon the first friction force and the second friction force.

3. The system of claim 1, wherein the controller is further configured to determine the hydraulic seal coefficient of friction while a piston of the hydraulic cylinder assembly moves at a generally constant rate.

4. The system of claim 3, wherein the generally constant rate is less than a predetermined rate.

5. The system of claim 3, wherein the linkage member is pivotally mounted and movement of the piston moves the linkage member along the path at a generally constant rate of less than approximately 2° per second.

6. The system of claim 1, wherein the controller is further configured to determine the hydraulic seal coefficient of friction while the linkage member moves a first path length along the path while determining the first friction force and a second path length along the path while determining the second friction force.

7. The system of claim 1, wherein the controller is further configured to receive a plurality of third load first direction force signals as the hydraulic cylinder assembly moves the linkage member along the path in the first direction and the linkage member engages a third load, receive a plurality of third load second direction force signals as the hydraulic cylinder assembly moves the linkage member along the path in the second direction and the linkage member engages the third load, determine a third friction force based at least in part upon a difference between the plurality of third load first direction force signals and the plurality of third load second direction force signals, and determine the hydraulic seal coefficient of friction based at least in part upon the first friction force, the second friction force, and the third friction force.

8. The system of claim 1, further including a second linkage member pivotally connected to the linkage member, and the controller is further configured to determine the hydraulic seal coefficient of friction while the linkage member is fixed relative to the second linkage member.

9. A controller implemented method of determining a hydraulic seal coefficient of friction of a hydraulic cylinder assembly, comprising:
receiving a plurality of first load first direction force signals as the hydraulic cylinder assembly moves a linkage member along a path in a first direction and the linkage member engages a first load;
receiving a plurality of first load second direction force signals as the hydraulic cylinder assembly moves the linkage member along the path in a second direction, the second direction being generally opposite the first direction;
determining a first friction force based at least in part upon a difference between the plurality of first load first direction force signals and the plurality of first load second direction force signals;
receiving a plurality of second load first direction force signals as the hydraulic cylinder assembly moves the linkage member along the path in the first direction and the linkage member engages a second load;
receiving a plurality of second load second direction force signals as the hydraulic cylinder assembly moves the linkage member along the path in the second direction and the linkage member engages the second load;
determining a second friction force based at least in part upon a difference between the plurality of second load first direction force signals and the plurality of second load second direction force signals;
receiving a plurality of third load first direction force signals as the hydraulic cylinder assembly moves the linkage member along the path in the first direction and the linkage member engages a third load;
receiving a plurality of third load second direction force signals as the hydraulic cylinder assembly moves the linkage member along the path in the second direction and the linkage member engages the third load;
determining a third friction force based at least in part upon a difference between the third load first direction force signals and the third load second direction force signals; and determining the hydraulic seal coefficient of friction based at least in part upon the first friction force, the second friction force; and
determining a hydraulic seal coefficient of friction based at least in part upon the first friction force, the second friction force, and the third friction force.

10. The method of claim 9, further including receiving a piston end cylinder pressure signal indicative of a piston end cylinder pressure of the hydraulic cylinder assembly and a rod end cylinder pressure signal indicative of a rod end cylinder pressure of the hydraulic cylinder assembly, and determining a piston end hydraulic seal coefficient of friction and a rod end hydraulic seal coefficient of friction.

11. The method of claim 10, further including determining a coefficient of Coulomb friction associated with the hydraulic cylinder assembly based at least in part upon the first friction force and the second friction force.

12. The method of claim 9, further including moving a piston of the hydraulic cylinder assembly at a generally constant rate while determining the hydraulic seal coefficient of friction.

13. The method of claim 12, wherein the generally constant rate is less than a predetermined rate.

14. The method of claim 12, wherein the linkage member is pivotally mounted and moving the piston moves the linkage member along the path at a generally constant rate of less than approximately 2° per second.

15. The method of claim 9, further including moving the linkage member a first path length along the path while determining the first friction force and moving the linkage member a second path length along the path while determining the second friction force while determining the hydraulic seal coefficient of friction.

16. The method of claim 9, including providing a second linkage member pivotally connected to the linkage member, and fixing the linkage member relative to the second linkage member while determining the hydraulic seal coefficient of friction.

17. A machine comprising:
prime mover;
a linkage member for moving a load, the linkage member being movable along a path;
a hydraulic cylinder assembly operatively connected to the linkage member for moving the linkage member along the path, the hydraulic cylinder assembly being operatively connected to the prime mover;
a force sensor configured to provide a force signal indicative of a force of the hydraulic cylinder assembly, the force sensor including a pressure sensor system configured to provide a piston end cylinder pressure signal indicative of a piston end cylinder pressure of the hydraulic cylinder assembly and a rod end cylinder pressure signal indicative of a rod end cylinder pressure of the hydraulic cylinder assembly; and
a controller configured to:
receive a plurality of first load first direction force signals as the hydraulic cylinder assembly moves the linkage member along the path in a first direction and the linkage member engages a first load;
receive a plurality of first load second direction force signals as the hydraulic cylinder assembly moves the linkage member along the path in a second direction, the second direction being generally opposite the first direction;

determine a first friction force based at least in part upon a difference between the plurality of first load first direction force signals and the plurality of first load second direction force signals;

receive a plurality of second load first direction force signals as the hydraulic cylinder assembly moves the linkage member along the path in the first direction and the linkage member engages a second load;

receive a plurality of second load second direction force signals as the hydraulic cylinder assembly moves the linkage member along the path in the second direction and the linkage member engages the second load;

determine a second friction force based at least in part upon a difference between the plurality of second load first direction force signals and the plurality of second load second direction force signals; and determine a piston end hydraulic seal coefficient of friction and a rod end hydraulic seal coefficient of friction based at least in part upon the first friction force and the second friction force.

* * * * *